United States Patent
Jiang et al.

(10) Patent No.: US 7,638,525 B2
(45) Date of Patent: Dec. 29, 2009

(54) TRISUBSTITUTED THIOPHENES AS PROGESTERONE RECEPTOR MODULATORS

(75) Inventors: Weiqin Jiang, Raritan, NJ (US); James J. Fiordeliso, Raritan, NJ (US); Zhihua Sui, Raritan, NJ (US)

(73) Assignee: Janssen Pharmaceutica N.V., Beerse (BE)

( * ) Notice: Subject to any disclaimer, the term of this patent is extended or adjusted under 35 U.S.C. 154(b) by 580 days.

(21) Appl. No.: 11/255,445

(22) Filed: Oct. 21, 2005

(65) Prior Publication Data

US 2006/0106047 A1 May 18, 2006

Related U.S. Application Data

(60) Provisional application No. 60/622,581, filed on Oct. 27, 2004.

(51) Int. Cl.
*A61K 31/4747* (2006.01)
*A61K 31/4545* (2006.01)
*C07D 409/14* (2006.01)

(52) U.S. Cl. .................. 514/278; 514/326; 546/171; 546/193; 546/212

(58) Field of Classification Search .................. 514/278, 514/326, 318; 546/17, 193, 212
See application file for complete search history.

(56) References Cited

U.S. PATENT DOCUMENTS 5,688,810 A 11/1997 Jones et al.

FOREIGN PATENT DOCUMENTS

| DE | 201306 Z | 7/1983 |
|---|---|---|
| WO | WO 00/66591 A1 | 11/2000 |
| WO | WO 03/018536 A1 | 3/2003 |

OTHER PUBLICATIONS fuchs Young et al. Inhibition of estrogen-stimulated . . . mol. Carcinogenesis 17:151-159 (1996).*
Liebschet et al. "5-acyl-3-aryl . . . " CA 100:51590 (1984).*
Liebscher et al. "Formylation products . . . " CA 99:105076(1983).*
Noack et al. "Synthesis and characterisation . . . " Tetrahedron v.58 p. 2137-2146 (2002).*
Noack, A. et al.: "Synthesis and characterisation of N,N-disubstituted 2-amino-5-acylthiophenes and 2-amino-5-acylthiazoles"; Tetrahedron 58 (2002) pp. 2137-2146.
Liebscher, Jurgen: "Reactions of 3-Amino and 3-Hydroxythioacrylamides with Alkylating Reagents-Synthesis of N,N-Disubstituted 2-Aminothiophenes", Journal f. prakt. Chemie. Band 325, Heft 1, 1983, S. 168-172.
PCT International Search Report for Int'l Appln. No. PCT/US2005/037827 dated Mar. 8, 2006.

* cited by examiner

*Primary Examiner*—Celia Chang

(57) ABSTRACT

The present invention is directed to novel trisubstituted thiophene derivatives, pharmaceutical compositions containing them and their use in the treatment or prevention of disorders and diseases mediated by agonists and antagonists of the progesterone receptor. The clinical usage of these compounds are related to hormonal contraception, the treatment and/or prevention of secondary dysmenorrhea, amenorrhea, dysfunctional uterine bleeding, uterine leiomyomata, endometriosis; polycystic ovary syndrome, carcinomas and adenocarcinomas of the endometrium, ovary, breast, colon or prostate. Additional uses of the invention include stimulation of food intake.

3 Claims, No Drawings

TRISUBSTITUTED THIOPHENES AS PROGESTERONE RECEPTOR MODULATORS

RELATED APPLICATION

This application claims the benefit of U.S. Provisional Application No. 60/622,581, filed Oct. 27, 2004, which is incorporated herein by reference in its entirety.

FIELD OF THE INVENTION

The present invention is directed to novel trisubstituted thiophene derivatives, pharmaceutical compositions containing them and their use in the treatment or prevention of disorders and diseases mediated by agonists and antagonists of the progesterone receptors. The clinical usage of these compounds are related to hormonal contraception, the treatment and/or prevention of secondary dysmenorrhea, amenorrhea, dysfunctional uterine bleeding, uterine leiomyomata, endometriosis; polycystic ovary syndrome, carcinomas and adenocarcinomas of the endometrium, ovary, breast, colon, prostate. Additional uses of the invention include stimulation of food intake.

BACKGROUND OF THE INVENTION

Intracellular receptors are a class of structurally related proteins involved in the regulation of gene proteins. Steroid receptors are a subset of these receptors, including the progesterone receptors (PR), androgen receptors (AR), estrogen receptors (ER), glucocorticoid receptors (GR) and mineralocorticoid receptors (MR). Regulation of a gene by such factors requires the intracellular receptor and a corresponding ligand which has the ability to selectively bind to the receptor in a way that affects gene transcription.

Progesterone receptor modulators (progestagens) are known to play an important role in mammalian development and homeostasis. Progesterone is known to be required for mammary gland development, ovulation and the maintenance of pregnancy. Currently, steroidal progestin agonists and antagonists are clinically approved for contraception, hormone replacement therapy (HRT) and therapeutic abortion. Moreover, there is good preclinical and clinical evidence for the value of progestin antagonists in treating endometriosis, uterine leiomyomata (fibroids), dysfunctional uterine bleeding and breast cancer.

The current steroidal progestagens have been proven to be quite safe and are well tolerated. Sometimes, however, side effects (e.g. breast tenderness, headaches, depression and weight gain) have been reported that are attributed to these steroidal progestagens, either alone or in combination with estrogenic compounds.

Steroidal ligands for one receptor often show cross-reactivity with other steroidal receptors. As an example, many progestagens also bind to glucocorticoid receptor. Non-steroidal progestagens have no molecular similarity with steroids and therefore one might also expect differences in physicochemical properties, pharmacokinetic (PK) parameters, tissue distribution (e.g. CNS versus peripheral) and, more importantly, non-steroidal progestagens may show no/less cross-reactivity to other steroid receptors. Therefore, non-steroidal progestagens will likely emerge as major players in reproductive pharmacology in the foreseeable future.

It was known that progesterone receptor existed as two isoforms, full-length progesterone receptor isoform (PR-B) and its shorter counterpart (PR-A). Recently, extensive studies have been implemented on the progesterone receptor knockout mouse (PRKO, lacking both the A- and B-forms of the receptors), the mouse knockoutting specifically for the PR-A isoform (PRAKO) and the PR-B isoform (PRBKO). Different phenotypes were discovered for PRKO, PRAKO and PRBKO in physiology studies in terms of fertility, ovulation uterine receptivity, uterine proliferation, proliferation of mammary gland, sexual receptivity in female mice, sexual activity in male mice and infanticide tendencies in male mice. These findings provided insights for synthetic chemists to construct not only selective progesterone receptor modulator (SPRM), but also PR-A or PR-B selective progesterone receptor modulator.

SUMMARY OF THE INVENTION

The present invention provides novel trisubstituted thiophenes of formula (I):

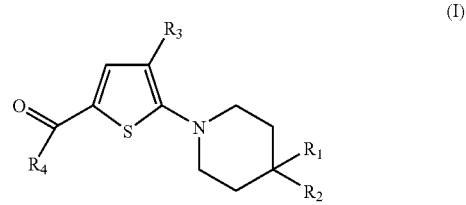

(I)

wherein $R_1$ and $R_2$ are independently selected from the group consisting of hydrogen, alkyl, alkoxy, cycloalkyl, aryl, aralkyl, heteroaryl and heteroaryl-alkyl; wherein the cycloalkyl, aryl, aralkyl, heteroaryl or heteroaryl-alkyl group is optionally substituted with one or more substituents independently selected from the group consisting of halogen, hydroxy, alkyl, alkoxy, —S(alkyl), —$SO_2R^C$, $NO_2$, CN, $CO_2H$, $R^C$, —$OR^C$, —$SO_2$—$NR^DR^E$, —$NR^DR^E$, -(alkyl)$_{0-4}$-(Q)$_{0-1}$-(alkyl)$_{0-4}$-C(O)—OR and $CF_3$;

wherein $R^C$ is selected from the group consisting of alkyl, cycloalkyl, cycloalkyl-alkyl, aryl, aralkyl, heteroaryl, heteroaryl-alkyl, heterocycloalkyl and heterocycloalkyl-alkyl;

wherein Q is selected from the group consisting of O, S, NH, N(alkyl) and —CH=CH—;

wherein $R^D$ and $R^E$ are each independently selected from the group consisting of hydrogen and alkyl; alternatively $R^D$ and $R^E$ are taken together with the nitrogen atom to which they are bound to form a 4 to 8 membered ring selected from the group consisting of heteroaryl or heterocycloalkyl; wherein the heteroaryl or heterocycloalkyl group is optionally substituted with one or more substituents independently selected from halogen, hydroxy, alkyl, alkoxy, carboxy, amino, alkylamino, dialkylamino, nitro, $CF_3$ or cyano;

wherein $R^F$ is selected from the group consisting of hydrogen, alkyl, cycloalkyl, cycloalkyl-alkyl, aryl, aralkyl, heteroaryl, heteroaryl-alkyl, heterocycloalkyl and heterocycloalkyl-alkyl; wherein the cycloalkyl, aryl, heteroaryl, heteroaryl-alkyl, heterocycloalkyl or heterocycloalkyl-alkyl group is optionally substituted with one or more substituents independently selected from halogen, hydroxy, alkyl, alkoxy, carboxy, amino, alkylamino, dialkylamino, $CF_3$ nitro or cyano;

alternatively, $R_1$ and $R_2$ are taken together with the carbon atom to which they are bound to form C(O), or to form a cycloalkyl or hetero-cycloalkyl.

$R_3$ is aryl or heteroaryl, optionally substituted by up to three of $R^5$; wherein R$_5$ is independently selected from the group consisting of halogen, hydroxy, R$^C$, amino, alkylamino, dialkylamino, nitro, cyano, CF$_3$, SO$_2$(alkyl), —C(O)R$^G$, —C(O)OR$^G$, —OC(O)R$^G$, —OSi(R$^G$)$_3$—OR$^G$, —SO$_2$N(R$^G$)$_2$, —O-(alkyl)$_{1-4}$-C(O)R$^G$ and —O-(alkyl)$_{1-4}$-C(O)OR$^G$;

wherein each R$^G$ is independently selected from hydrogen, alkyl, aryl, aralkyl; wherein the alkyl, aryl or aralkyl group is optionally substituted with one or more substituents independently selected from alkyl, halogenated alkyl, alkoxy, halogen, hydroxy, nitro, cyano, —OC(O)-alkyl or —C(O)O-alkyl;

alternatively two R$^G$ groups are taken together with the nitrogen atom to which they are bound to form a heterocycloalkyl group; wherein the heterocycloalkyl group is optionally substituted with one or more substituents independently selected from halogen, hydroxy, alkyl, alkoxy, carboxy, amino, alkylamino, dialkylamino, nitro or cyano;

R$_4$ is alkyl, aryl or heteroaryl, wherein the aryl or heteroaryl are optionally substituted with up to three R$_5$;

or a pharmaceutically acceptable salt thereof.

Illustrative of the invention is pharmaceutical composition comprising a pharmaceutically acceptable carrier and any of the compounds described above. An illustration of the invention is a pharmaceutical composition made by mixing any of the compounds described above and a pharmaceutically acceptable carrier. Illustrating the invention is process for making a pharmaceutical composition comprising mixing any of the compounds described above and a pharmaceutically acceptable carrier.

Exemplifying the invention are methods of treating a disorder mediated by one or more progesterone receptors in a subject in need thereof comprising administering to the subject a therapeutically effective amount of any of the compounds or pharmaceutical compositions described above.

Illustrating the invention is a method of contraception comprising administering to a subject in need thereof co-therapy with a therapeutically effective amount of a compound of formula (I) with an estrogenic compound.

Another example of the invention is the use of any of the compounds described herein in the preparation of a medicament for treating: (a) dysfunctional bleeding, (b) endometriosis, (c) uterine leiomyomata, (d) secondary amenorrhea, (e) polycystic ovary syndrome, (f) carcinomas and adenocarcinomas of the endometrium, ovary, breast, colon, prostate, (g) stimulation of food intake in a subject in need thereof.

DETAILED DESCRIPTION OF THE INVENTION

The present invention is directed to a compound of formula (I):

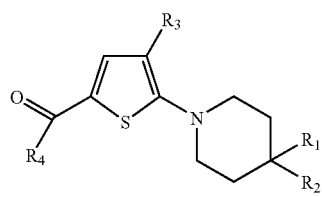

(I)

wherein R$_1$, R$_2$, R$_3$ and R$_4$ are as herein defined, useful for the treatment of disorders mediated by progesterone receptors. More particularly, the compounds of the present invention are useful for the treatment and prevention of disorders mediated by the progesterone-A and progesterone-B receptors. More preferably, the compounds of the present invention are tissue selective progesterone receptor modulators.

The progesterone receptor antagonists of this invention, used alone or in combination with an estrogenic compound, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-dependent tumors. Additional uses of the present progesterone receptor antagonists include the synchronization of the estrus in livestock.

The progesterone receptor agonists of this invention, used alone or in combination, can be utilized in methods of contraception and the treatment and/or prevention of dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

In an embodiment of the invetion, R$_1$ and R$_2$ are taken together with the carbon atom to which they are bound to form C(O), or to form a cycloalkyl or hetero-cycloalkyl.

In another embodiment, R$_3$ is selected from the group consisting of aryl, thienyl and pyridinyl In another embodiment, R$_4$ is substituted aryl.

In yet another embodiment of the present invention, R$_4$ is C$_{1-8}$ alkyl.

In an embodiment of the present invention are compounds of formula (I) wherein R$_3$ is 4-pyridinyland R$_4$ is aryl, heteroaryl, substituted aryl, substituted heteroaryl or C$_{1-4}$ alkyl.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, acetate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

As used herein, the term "progestogen antagonist" shall include mifepristone, J-867 (Jenapharm/TAP Pharmaceuticals), J-956 (Jenapharm/TAP Pharmaceuticals), ORG-31710 (Organon), ORG-33628 (Organon), ORG-31806 (Organon), onapristone and PRA248 (Wyeth).

As used herein, unless otherwise noted, "halogen" shall mean chlorine, bromine, fluorine and iodine.

As used herein, unless otherwise noted, the term "alkyl" whether used alone or as part of a substituent group, includes straight and branched chain compositions of one to eight carbon atoms. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms. Similarly, the group "-(alkyl)$_{0-4}$-", whether alone or as part of a large substituent group, shall mean the absence of an alkyl group or the presence of an alkyl group comprising one to four carbon atoms. Suitable examples include, but are not limited to —CH$_2$—, —CH$_2$CH$_2$—, CH$_2$—CH(CH$_3$)—, CH$_2$CH$_2$CH$_2$—, —CH$_2$CH(CH$_3$) CH$_2$—, CH$_2$CH$_2$CH$_2$CH$_2$—, and the like.

As used herein, unless otherwise noted, "alkoxy" shall denote an oxygen ether radical of the above described straight or branched chain alkyl groups. For example, methoxy, ethoxy, n-propoxy, sec-butoxy, t-butoxy, n-hexyloxy and the like.

As used herein, unless otherwise noted, "aryl" shall refer to unsubstituted carbocyclic aromatic groups such as phenyl, naphthyl, and the like.

As used herein, unless otherwise noted, "aralkyl" shall mean any lower alkyl group substituted with an aryl group such as phenyl, naphthyl and the like. Suitable examples include benzyl, phenylethyl, phenylpropyl, naphthylmethyl, and the like.

As used herein, unless otherwise noted, the term "cycloalkyl" shall mean any stable 3-8 membered monocyclic, saturated ring system, for example cyclopropyl, cyclobutyl, cyclopentyl, cyclohexyl, cycloheptyl and cyclooctyl.

As used herein, unless otherwise noted, the term "cycloalkyl-alkyl" shall mean any lower alkyl group substituted with a cycloalkyl group. Suitable examples include, but are not limited to cyclohexyl-methyl, cyclopentyl-methyl, cyclohexyl-ethyl, and the like.

As used herein, unless otherwise noted, the terms "acyloxy" shall mean a radical group of the formula —O—C(O)—R where R is alkyl, aryl or aralkyl, wherein the alkyl, aryl or aralkyl is optionally substituted. As used herein, the term "carboxylate" shall mean a radical group of the formula —C(O)O—R where R is alkyl, aryl or aralkyl, wherein the alkyl, aryl or aralkyl is optionally substituted.

As used herein, unless otherwise noted, "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure.

As used herein, unless otherwise noted, the term "heteroaryl-alkyl" shall mean any lower alkyl group substituted with a heteroaryl group. Suitable examples include, but are not limited to pyridyl-methyl, isoquinolinyl-methyl, thiazolyl-ethyl, furyl-ethyl, and the like.

As used herein, the term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure.

Examples of suitable heteroaryl groups include, but are not limited to, pyrrolinyl, pyrrolidinyl, dioxalanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, and the like.

As used herein, unless otherwise noted, the term "heterocycloalkyl-alkyl" shall mean any lower alkyl group substituted with a heterocycloalkyl group. Suitable examples include, but are not limited to piperidinyl-methyl, piperazinyl-methyl, piperazinyl-ethyl, morpholinyl-methyl, and the like.

When a particular group is "substituted" (e.g., cycloalkyl, aryl, heteroaryl, heterocycloalkyl), that group may have one or more substituents, preferably from one to five substituents, more preferably from one to three substituents, most preferably from one to two substituents, independently selected from the list of substituents. Additionally when aralkyl, heteroaryl-alkyl, heterocycloalkyl-alkyl or cycloalkyl-alkyl group is substituted, the substituent(s) may be on any portion of the group (i.e. the substituent(s) may be on the aryl, heteroaryl, heterocycloalkyl, cycloalkyl or the alkyl portion of the group.)

With reference to substituents, the term "independently" means that when more than one of such substituents is possible, such substituents may be the same or different from each other.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

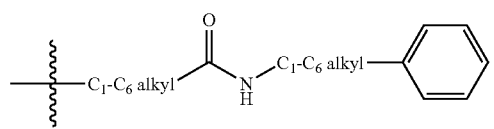

Abbreviations used in the specification, particularly the Schemes and Examples, are as follows
Ac=Acetyl group (—C(O)—CH₃)
DCM=Dichloromethane
DIPEA or DIEA Diisopropylethylamine
DMAP=N,N-Dimethylaminopyridine
DMF=Dimethyl formamide
ERT=Estrogen replacement therapy
Et=ethyl (i.e. —CH₂CH₃)
EtOAc=Ethyl acetate
FBS=Fetal bovine serum
HPLC=High pressure liquid chromatography
HRT=Hormone replacement therapy
LHMDS or LiHMDS or=Lithium Hexamethyldisilazinamide
(TMS)₂NLi or LiN(TMS)₂
MeOH=Methanol
Ph=Phenyl
PPTS=Pyridinium p-toluenesulfonate
TBAF=Tetra(n-butyl)ammonium fluoride
TBDMS=Tert-butyldimethylsilane
TBS=Tert-butyl-dimethyl-silyl
TBSCl=Tert-butyl-dimethyl-silyl chloride
pTEA or Et₃N=Triethylamine
TFA=Trifluoroacetic acid
THF=Tetrahydrofuran
TMS=Trimethylsilyl
TsOH=Tosic acid The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. Wherein the present invention directed to co-therapy comprising administration of one or more compound(s) of formula I and a progestogen or progestogen antagonist, "therapeutically effective amount" shall mean that amount of the combination of agents taken together so that the combined effect elicits the desired biological or medicinal response. For example, the therapeutically effective amount of co-therapy comprising administration of a compound of formula I and progestogen would be the amount of the compound of formula I and the amount of the progestogen that when taken together or sequentially have a combined effect that is therapeutically effective. Further, it will be recognized by one skilled in the art that in the case of co-therapy with a therapeutically effective amount, as in the example above, the amount of the compound of formula I and/or the amount of the progestogen or progestogen antagonist individually may or may not be therapeutically effective.

As used herein, the term "co-therapy" shall mean treatment of a subject in need thereof by administering one or more compounds of formula I with a progestogen or progestogen antagonist, wherein the compound(s) of formula I and progestogen or progestogen antagonist are administered by any suitable means, simultaneously, sequentially, separately or in a single pharmaceutical formulation. Where the compound(s) of formula I and the progestogen or progestogen antagonist are administered in separate dosage forms, the number of dosages administered per day for each compound may be the same or different. The compound(s) of formula I and the progestogen or progestogen antagonist may be administered via the same or different routes of administration. Examples of suitable methods of administration include, but are not limited to, oral, intravenous (iv), intramuscular (im), subcutaneous (sc), transdermal, and rectal. Compounds may also be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices. The compound(s) of formula I and the progestogen or progestogen antagonist may be administered according to simultaneous or alternating regimens, at the same or different times during the course of the therapy, concurrently in divided or single forms.

As used herein, the term "composition" is intended to encompass a product comprising the specified ingredients in the specified amounts, as well as any product which results, directly or indirectly, from combinations of the specified ingredients in the specified amounts.

Compounds of formula (I) wherein R3 is 4-pyridyl, R4 is aryl and R1 and R2 is O may be prepared according to the processes outlined in Scheme 1.

More particularly, a suitably substituted compound of formula (II), where X and Y are O or S, a known compound or compound prepared by known methods, is reacted with a compound of formula (III), a known compound, in the presence of an organic acid such as acetic acid, p-TSA, oxalic acid and the

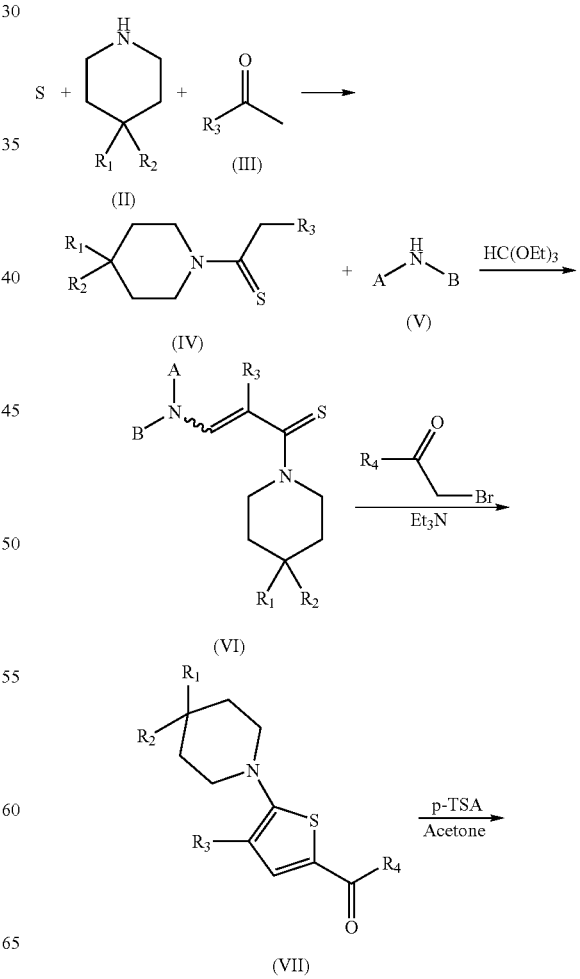

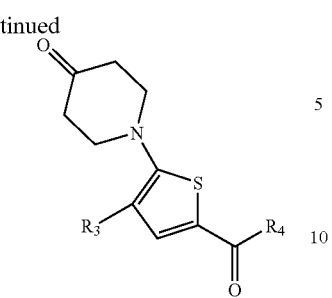

(VIII)

When R1, R2 = alkoxy group like, in an organic solvent such as THF, 1,4-dioxlane, ethyl ether, and the like, at a temperature in the range of 0 to 25° C. to yield the corresponding compound of formula (IV). The condensation of compound II and III with sulfur to yield compound IV can be effected by various coupling reactions including Willgerodt-Kindler Reaction.

The compound of formula (IV) is reacted with a suitably substituted compound of formula (V), a known cyclic or normal secondary amine, in the presence of $HC(OEt)_3$ or $HC(OMe)_3$ at a temperature in the range of 0 to 250° C. to yield the corresponding compound of formula (VI).

Accordingly, the compound of formula (VI) is reacted with a suitably substituted bromoketone, in the presence of an organic base, such as triethyl amine, duisopropyl ethyl amine, pyridine and the like; or inorganic base, such as $K_2CO_3$, $Na_2CO_3$ and the like, in an organic solvent such as MeOH, toluene, benzene, THF, methylene chloride, at an elevated temperature in the range of 25 to 150° C. to yield the corresponding compound of formula (VII).

The compound of formula (VII) is deprotected to yield compound of formula (VIII) in the presence of organic protic acid, such as acetic acid, camphor sulfonic acid, p-TSA, oxalic acid and the like in an organic solvent, such as acetone, THF, 1,4-dioxane and the like.

One skilled in the art will recognize that it may be necessary and/or desirable to protect one or more of the $R^1$, $R^2$ and/or $R^3$, $R^4$ groups at any of the steps within the process described above. This may be accomplished using known protecting groups and know protection and de-protection reagents and conditions, for example such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991.

TABLE 1

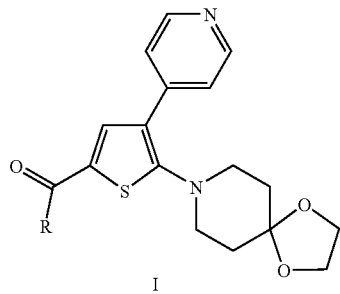

I

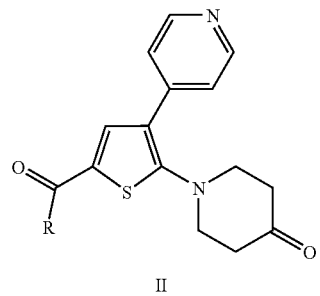

II

| Example # | Structure or II | R | MF |
|---|---|---|---|
| 1 | I | 3,4-di-Cl-phenyl | $C_{23}H_{20}C_{12}N_2O_3S$ |
| 2 | I | 4-F-phenyl | $C_{23}H_{21}FN_2O_3S$ |
| 3 | I | 4-Cl-phenyl | $C_{23}H_{21}ClN_2O_3S$ |
| 4 | I | 4-$NO_2$-phenyl | $C_{23}H_{21}N_3O_5S$ |
| 5 | I | Et | $C_{19}H_{22}N_2O_3S$ |
| 6 | I | Phenyl | $C_{23}H_{22}N_2O_3S$ |
| 7 | I | 3-MeO-phenyl | $C_{24}H_{24}N_2O_4S$ |
| 8 | I | 3,5-di-$CF_3$-phenyl | $C_{25}H_{20}F_6N_2O_3S$ |
| 9 | I | 2-MeO-phenyl | $C_{24}H_{24}N_2O_4S$ |
| 10 | I | 3-Br-phenyl | $C_{23}H_{21}BrN_2O_3S$ |
| 11 | II | Phenyl | $C_{21}H_{18}N_2O_2S$ |
| 12 | II | 3-MeO-phenyl | $C_{22}H_{20}N_2O_3S$ |
| 13 | II | 4-F-phenyl | $C_{21}H_{17}FN_2O_2S$ |
| 14 | II | 3,5-di-$CF_3$-phenyl | $C_{23}H_{16}F_6N_2O_2S$ |
| 15 | II | 2-MeO-phenyl | $C_{22}H_{20}N_2O_3S$ |
| 16 | II | 4-Cl-phenyl | $C_{21}H_{17}ClN_2O_2S$ |
| 17 | II | 4-$NO_2$-phenyl | $C_{21}H_{17}N_3O_4S$ |
| 18 | II | Et | $C_{17}H_{18}N_2O_2S$ |
| 19 | II | 3-$NO_2$-phenyl | $C_{21}H_{17}N_3O_4S$ |
| 20 | II | 3-Br-phenyl | $C_{21}H_{17}BrN_2O_2S$ |

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The compounds of the present invention can be used in the form of salts derived from pharmaceutically or physiologically acceptable acids or bases. These salts include, but are not limited to, the following salts with inorganic acids such as hydrochloric acid, sulfuric acid, nitric acid, phosphoric acid and as the case may be, such organic acids as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

This invention includes pharmaceutical compositions comprising one or more compounds of this invention, preferably in combination with one or more pharmaceutically acceptable carriers and/or excipients. The invention also includes methods of contraception and methods of treating or preventing maladies associated with the progesterone receptor, the methods comprising administering to a mammal in need thereof a pharmaceutically effective amount of one or more compounds as described above wherein R4 is alkyl, aryl, heteroary or alkylaryl groupl.

The progesterone receptor antagonists of this invention, used alone or in combination with estrogen or partial estrogen antagonist, can be utilized in methods of contraception and the treatment and/or prevention of benign and malignant neoplastic disease. Specific uses of the compounds and pharmaceutical compositions of invention include the treatment and/or prevention of uterine myometrial fibroids, endometriosis, benign prostatic hypertrophy; carcinomas and adenocarcinomas of the endometrium, ovary, breast, colon, prostate, pituitary, meningioma and other hormone-depent tumors. Additional uses of the present progesterone receptor antagonists include the synchronization of the estrus in livestock.

When used in contraception the progesterone receptor antagonists of the current invention may be used either alone in a continuous administration of between 0.1 and 500 mg per day, or alternatively used in a different regimen which would entail 2-4 days of treatment with the progesterone receptor antagonist after 21 days of a progestin. In this regimen between 0.1 and 500 mg daily doses of the progestin (e.g. levonorgestrel, trimegestone, gestodene, norethindrone acetate, norgestimate or cyproterone acetate) would be followed by between 0.1 and 500 mg daily doses of the progesterone receptor antagonists of the current invention.

The progesterone receptor agonists of this invention, used alone or in combination, can also be utilized in methods of contraception and the treatment and/or prevention of dysfunctional bleeding, uterine leiomyomata, endometriosis; polycystic ovary syndrome, carcinomas and adenocarcinomas of the endometrium, ovary, breast, colon, prostate. Additional uses of the invention include stimulation of food intake.

When used in contraception the progesterone receptor agonists of the current invention are preferably used in combination or sequentially with an estrogen agonist (e.g. ethinyl estradiao). The preferred dose of the progesterone receptor agonist is 0.01 mg and 500 mg per day.

This invention also includes pharmaceutical compositions comprising one or more compounds described herein, preferably in combination with one or more pharmaceutically acceptable carriers or excipients. When the compounds are employed for the above utilities, they may be combined with one or more pharmaceutically acceptable carriers, or excipients, for example, solvents, diluents and the like and may be administered orally in such forms as tablets, caplules, dispersible powders, granules, or suspensions containing, for example, from about 0.05 to 5% of suspending agent, syrups containing, for example, from about 10 to 50% of sugar, and elixirs containing, for example, from 20 to 50% ethanol, and the like, or in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.01 to about 500 mg/kg of animal body weight, preferably given in dual doses two to four times a day, or in a sustained release form. For most large mammals, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

These active compounds may be administered orally as well as by intravenous, imtramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oil, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxylpropylcellulose. Dispersions can also be prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions of dispersions. In all cases, the form must be sterile and must be fluid to the extent that easy syringe ability exits. It must be stable under conditions of manufacture and storage and must be preserved against the contaminating action of microorganisms such as bacterial and fungi. The carrier can be a solvent or dispersion medium containing, for example, water, ethanol (e.g., glycerol, propylene glycol and liquid polyethylene glycol), suitable mixtures thereof, and vegetable oil.

The following non-limiting examples illustrate preparation and use of the compounds of the invention.

EXAMPLE 1

A. 1-(1,4-Dioxa-8-aza-spiro[4.5]-dec-8-yl)-2-pyridin-4-yl-ethanethione

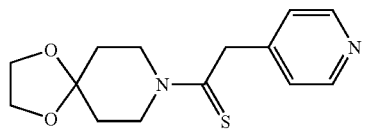

1-Pyridin-4-yl-ethanone (12.1 g, 0.1 mole), sulfur (3.36 g, 0.105 mol) and 1,4-dioxa-8-aza-spiro[4.5]decane were mixed with p-toluene sulfonic acid (0.50 g, 2.8 mmole) and heated to 120° C. for 3 hours. The slurry was poured into MeOH (50 mL). A bright yellow solid precipitated out. This was filtered and washed with another 20 mL of MeOH. The solid was dried to provide the product (24 g, 86.3%). $^1$H NMR (CD$_3$OD) δ 8.41 (m, 2H), 7.42 (m, 2H), 4.35 (m, 4H), 3.91 (m, 4H), 3.78 (m, 2H), 1.80 (m, 2H), 1.48 (m, 2H). MS (m/z): 279 (MH$^+$).

B. 1-(1,4-Dioxa-8-aza-spiro[4.5]-dec-8-yl)-3-morpholin-4-yl-2-pyridin-4-yl-propenethione

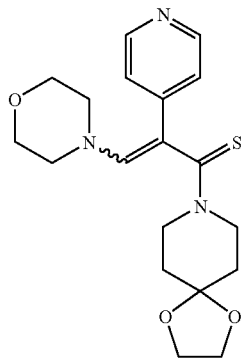

1-(1,4-Dioxa-8-aza-spiro[4.5]dec-8-yl)-2-pyridin-4-yl-ethanethione (20 g, 72 mmol), HC(OEt)$_3$ (21.3 g, 144 mol), morpholine (48 g, 55 mmol) was stirred at 125° C. for 4 hours. The solvent and excess reagent were distilled out at 100° C. under house vacumm. A yellow precipitate came out. After 30 min at 0° C., the precipitate was collected and washed with water (10 mL) and dried overnight under air suction to provide the product (20 g, 54%). $^1$H NMR (CDCl$_3$) δ 8.32 (m, 2H), 7.02 (m, 2H), 6.40 (s, 1H), 4.61 (m, 1H), 4.30 (m, 1H), 3.98 (m, 4H), 3.70 (m, 6H), 3.5 (s, 4H), 3.20 (m, 2H), 2.10 (m, 1H), 1.80 (m, 2H). MS (m/z): 376 (MH$^+$).

C. (3,4-Dichloro-phenyl)-[5-(1,4-dioxa-8-aza-spiro[4.5]-dec-8-yl)-4-pyridin-4-yl-thiophen-2-yl]-methanon

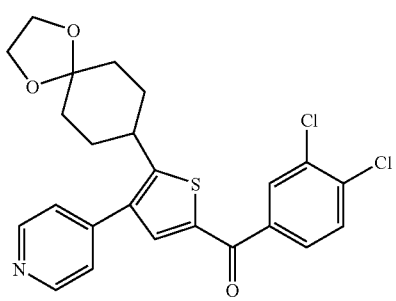

1-(1,4-Dioxa-8-aza-spiro[4.5]dec-8-yl)-3-morpholin-4-yl-2-pyridin-4-yl-propenethione (75 mg, 0.020 mmol), 2-bromo-1-(3,4-dichloro-phenyl)-ethanone (67 mg, 0.020 mmol) was stirred in MeOH (1 mL) with Et$_3$N (21 mg, 0.02 ml) for 4 hours at 65° C. This was diluted with EtOAc (20 mL) and washed with brine three times. The residue was purified by a preparative silica gel plate (5% MeOH/CH$_2$Cl$_2$) to provide product as a yellow solid (33 mg, 35%). $^1$H NMR (CDCl$_3$) δ 8.6 (m, 2H), 7.81 (s, 1H), 7.61-7.47 (m, 5H), 3.72 (m, 3.56 (m, 3H), 3.52 (s, 4H), 3.41 (m, 1H), 3.23 (m, 4H), 1.82 (m, 4H). MS (m/z): 475 (MH$^+$).

EXAMPLE 2

[5-(1,4-Dioxa-8-aza-spiro[4.5]-dec-8-yl)-4-pyridin-4-yl-thiophen-2-yl]-(4-fluoro-phenyl)-methanone

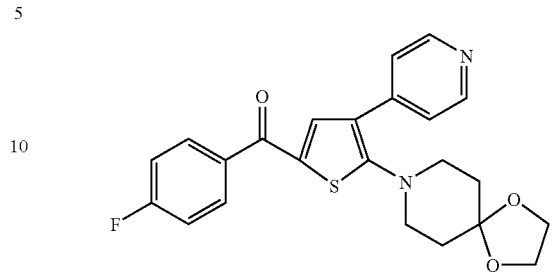

The title product was prepared in 33% yield according to the procedure described in Example 1c using 1-(1,4-dioxa-8-aza-spiro[4.5]dec-8-yl)-3-morpholin-4-yl-2-pyridin-4-yl-propenethione and 2-bromo-1-(4-fluoro-phenyl)-ethanone as starting material. $^1$H NMR (CDCl$_3$) δ 8.61 (dd, J=1.5 and 4.6 Hz, 5 2H), 7.86-7.83 (m, 2H), 7.53-7.50 (m, 3H), 7.20-7.15 (m, 2H), 3.98 (s, 4H), 3.23 (t, J=5.7 Hz, 4H), 1.83 (t, J=5.7 Hz, 4H); MS (m/z): 425 (MH$^+$).

EXAMPLE 3

(4-Chloro-phenyl)-[5-(1 4-dioxa-8-aza-spiro[4.5]-dec-8-yl)-4-pyridin-4-yl-thiophen-2-yl]-methanone

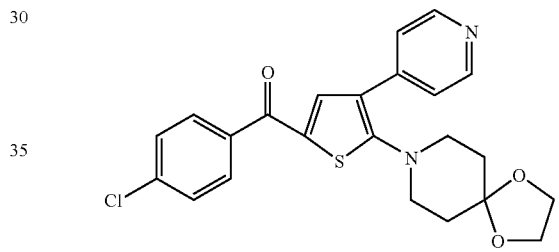

The title product was prepared in 29% yield according to the procedure described in Example 1c using 1-(1,4-dioxa-8-aza-spiro[4.5]dec-8-yl)-3-morpholin-4-yl-2-pyridin-4-yl-propenethione (374.5 mg, 1 mmol), 2-bromo-1-(4-chlorophenyl)-ethanone (233 mg, 1 mmol) as starting material. $^1$H NMR (CDCl$_3$) δ 8.62-8.58 (m, 2H), 7.78-7.74 (m, 2H), 7.52-7.45 (m, 5H), 3.98 (s, 1H), 3.24 (t, J=5.7 Hz, 4H), 1.83 (t, J=5.8 Hz, 4H); MS (m/z): 441 (MH$^+$); HRMS: calc'd MH$^+$ for C$_{23}$H$_{21}$ClN$_2$O$_3$S 441.1039; found 441.1025.

EXAMPLE 4

[5-(1 4-Dioxa-8-aza-spiro[4.5]-dec-8-yl)-4-pyridin-4-yl-thiophen-2-yl]-(4-nitro-phenyl)-methanone

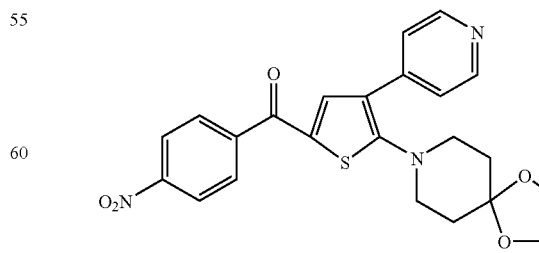

The title product was prepared in 18% yield according to the procedure described in Example 1c using 1-(1,4-dioxa-8- aza-spiro[4.5]dec-8-yl)-3-morpholin-4-yl-2-pyridin-4-yl-propenethione (374.5 mg, 1 mmol), 2-bromo-1-(4-nitro-phenyl)-ethanone (244 mg, 1 mmol) as starting material. $^1$H NMR (CDCl$_3$) δ 8.61 (dd, J=1.6 and 4.5 Hz, 2H), 8.36-8.33 (m, 2H), 7.95-7.92 (m, 2H), 7.47-7.46 (m, 3H), 3.99 (s, 4H), 3.27 (t, J=5.7 Hz, 4H), 1.83 (t, J=5.7 Hz, 4H); MZ (m/e): 452 (MH$^+$). HRMS: calc'd MH$^+$ for C$_{23}$H$_{21}$N$_3$O$_5$S 452.1280. Found 452.1286

EXAMPLE 5

1-[5-(1,4-Dioxa-8-aza-spiro[4.5]-dec-8-yl)-4-pyridin-4-yl-thiophen-2-yl]-1-one

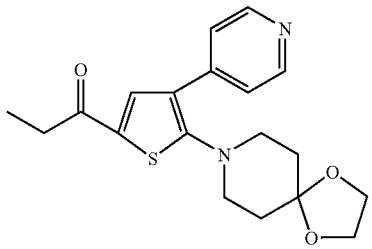

The title product was prepared in 22% yield as a white solid according to the procedure described in Example 1c using 1-(1,4-dioxa-8-aza-spiro[4.5]dec-8-yl)-3-morpholin-4-yl-2-pyridin-4-yl-propenethione (374.5 mg, 1 mmol), 1-bromo-butan-2-one (90%, 0.11 mL, 1 mmol) as starting material. $^1$H NMR (CDCl$_3$) δ 8.62 (dd, J=1.5 and 4.6 Hz, 2H), 7.65 (s,1H), 7.55 (dd, J=1.5 and 4.6 Hz, 2H), 3.97 (s, 4H), 3.17 (t, J=5.7 Hz, 4H), 2.85 (q, J=7.4 Hz, 2H), 1.82 (t, J=5.7 Hz, 4H), 1.23 (t, J=7.4 Hz, 3H). MS (m/z): 359 (MH$^+$); HRMS: Calc'd MH+for C$_{19}$H$_{22}$N$_2$O$_3$S 359.1429. Found 359.1420

EXAMPLE 6

[5-(1,4-Dioxa-8-aza-spiro[4.5]-dec-8-yl)-4-pyridin-4-yl-thiophen-2-yl]-phenyl-methanone

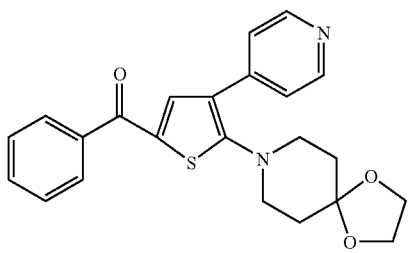

The title product was prepared in 28% yield as a yellow solid according to the procedure described in Example 1c using 2-bromo-1-phenyl-ethanone as starting material. $^1$H NMR (CDCl$_3$) δ 8.56 (m, 2H), 7.75 (m, 2H), 7.5 (m, 6H), 4.01 (s, 4H), 3.23 (m, 4H), 1.88 (m, 4H); MS (m/z): 407 (MH$^+$); HRMS: Calc'd MH$^+$ for C$_{23}$H$_{22}$N$_2$O$_3$S 407.1429. Found 407.1436.

EXAMPLE 7

[5-(1,4-Dioxa-8-aza-spiro[4.5]-dec-8-yl)-4-pyridin-4-yl-thiophen-2-yl-](3-methoxy-phenyl)-methanone

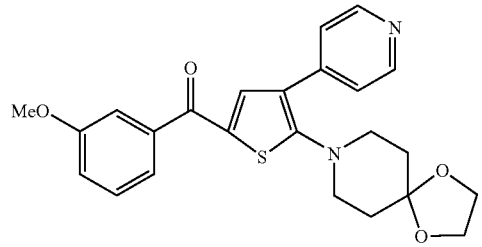

The title product was prepared in 24% yield as a yellow solid according to the procedure described in Example 1 c using 2-bromo-1-(3-methoxy-phenyl)-ethanone as starting material. $^1$H NMR (CDCl$_3$) δ 8.65 (m, 2H), 7.59-7.10(m, 7H), 3.95 (s, 4H), 3.25 (m, 4H), 1.82 (m, 4H); MS (m/z): 437 (MH$^+$); HRMS: calc'd MH$^+$ for C$_{24}$H$_{24}$N$_2$O$_4$S 437.1535. Found 437.1534.

EXAMPLE 8

(3,5-Bis-trifluoromethyl-phenyl)-[5-(1 4-dioxa-8-aza-spiro[4.5]-dec-8-yl)-4-pyridin-4-yl-thiophen-2-yl]-methanone

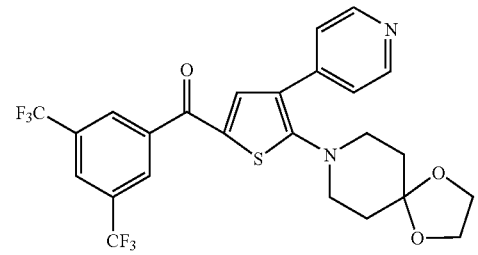

The title product was prepared in 18% yield according to the procedure described in Example 1c using 1-(3,5-bis-trifluoromethyl-phenyl)-2-bromo-ethanone as starting material. $^1$H NMR (CDCl$_3$) δ 8.60-7.39 (m, 7H), 3.95 (s, 4H), 3.28 (m, 4H), 1.82 (m, 4H); MS (m/z): 543 (MH$^+$); HRMS: calc'd MH$^+$ for C$_{25}$H$_{20}$F$_6$N$_2$O$_3$S 543.1177; found 543.1157.

EXAMPLE 9

[5-(1,4-Dioxa-8-aza-spiro[4.5]-dec-8-yl)-4-pyridin-4-yl-thiophen-2-yl]-(2-methoxy-phenyl)-methanone

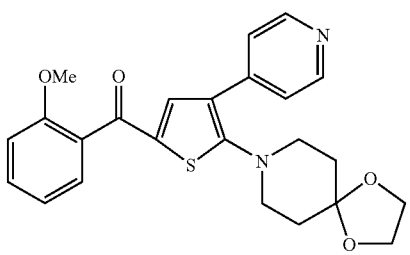

The title product was prepared in 23% yield according to the procedure described in Example 1c using 1-(2-methoxyphenyl)-2-bromo-ethanone as starting material. $^1$H NMR (CDCl$_3$) δ 8.55 (m, 2H), 7.45-7.30(m, 7H), 6.95 (m, 2H), 3.95 (s, 4H), 3.21 (m, 4H), 1.81 (m, 4H); MS (m/z): 437 (MH$^+$); HRMS: calc'd MH$^+$ for C$_{24}$H$_{24}$N$_2$O$_4$S 437.1535; found 437.1541.

EXAMPLE 10

(3-Bromo-phenyl)-[5-(1,4-dioxa-8-aza-spiro[4.5]-dec-8-yl)-4-pyridin-4-yl-thiophen-2-yl]-methanone

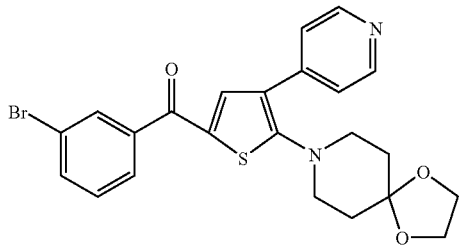

The title product was prepared in 25% yield according to the procedure described in Example 1c using 1-(3,5-bis-trifluoromethyl-phenyl)-2-bromo-ethanone as starting material. $^1$H NMR (CDCl$_3$) δ 8.61 (m, 2H), 7.91-7.31 (m, 7H), 3.94 (s, 4H), 3.23 (m, 4H), 1.81 (m, 4H); MS (m/z): 485, 487 (MH$^+$); HRMS: calc'd MH$^+$ for C$_{23}$H$_{21}$BrN$_2$O$_3$S 485.0534. Found 485.0514.

EXAMPLE 11

1-(5-Benzoyl-3-pyridin-4-yl-thiophen-2-yl)-piperidin-4-one

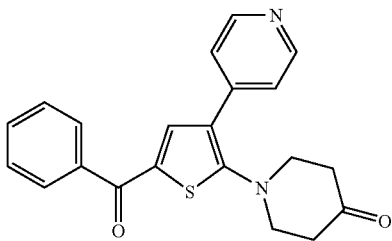

A solution of [5-(1,4-dioxa-8-aza-spiro[4.5]dec-8-yl)-4-pyridin-4-yl-thiophen-2-yl]-phenyl-methanone (39.5 mg, 0.097 mmole), p-toluenesulfonic acid monohydrate (37 mg, 0.194 mmole, 2 eq.), acetone (2 mL), and water (1 mL) was heated to reflux overnight. The solution was diluted with water and made basic to pH 14 with 4N sodium hydroxide or 1 M sodium carbonate solution. The solution was extracted twice with ethyl acetate. The organic extracts were dried over magnesium sulfate, filtered, and purified by column chromatography to provide the product as yellow solid (22 mg, 63%). $^1$H NMR (CDCl$_3$) δ 8.61 (m, 2H), 7.81-7.45 (m, 8H), 3.46 (m, 4H), 2.52 (m, 4H). MS (m/z): 363 (MH$^+$), 385 (MNa$^+$).

EXAMPLE 12

1-[5-(3-Methoxy-benzoyl)-3-pyridin-4-yl-thiophen-2-yl]-piperidin-4-one

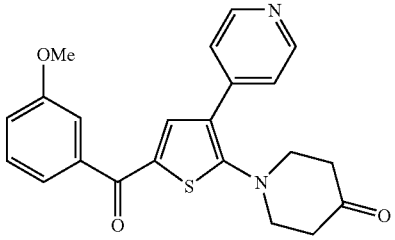

The title product was prepared in 73% yield according to the procedure described in Example 11 using [5-(1,4-dioxa-8-aza-spiro[4.5]dec-8-yl)-4-pyridin-4-yl-thiophen-2-yl]-(3-methoxy-phenyl)-methanone as starting material. $^1$H NMR (CDCl$_3$) δ 8.65 (m, 2H), 7.51-7.12 (m, 9H), 3.42 (m, 4H), 2.62 (m, 4H); Ms (m/z): 393 (MH$^+$), 391 (MH$^-$); HRMS: calc'd MH$^+$ for C$_{22}$H$_{20}$N$_2$O$_3$S 393.1273. Found 393.1280.

EXAMPLE 13

1-[5-(4-Fluoro-benzoyl)-3-pyridin-4-yl-thiophen-2-yl]-piperidin-4-one

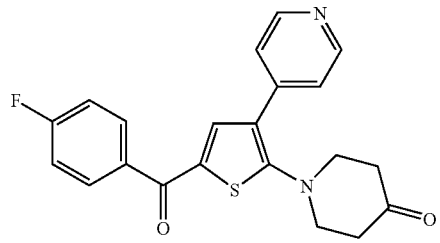

The title product was prepared in 69% yield according to the procedure described in Example 11 using [5-(1,4-dioxa-8-aza-spiro[4.5]dec-8-yl)-4-pyridin-4-yl-thiophen-2-yl]-(4-fluoro-phenyl)-methanone as starting material. $^1$H NMR (CDCl$_3$) δ 8.62-7.11 (m, 9H), 3.42 (m, 4H), 2.61 (m, 4H); MS (m/z): 413 (MNa$^+$), 379 (MH$^-$); HRMS: calc'd MH$^+$ for C$_{21}$H$_{17}$FN$_2$O$_2$S 381.1073. Found 381.1080.

EXAMPLE 14

1-[5-(3,5-Bis-trifluoromethyl-benzoyl)-3-pyridin-4-yl-thiophen-2-yl]-piperidin-4-one

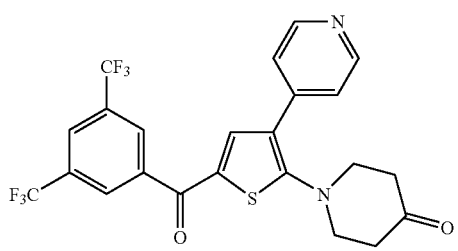

The title product was prepared in 33% yield as a yellow solid according to the procedure described in Example 11 using (3,5-bis-trifluoromethyl-phenyl)-[5-(1,4-dioxa-8-aza-spiro[4.5]dec-8-yl)-4-pyridin-4-yl-thiophen-2-yl]-methanone as starting material. $^1$H NMR (CDCl$_3$) δ 8.65-7.42 (m, 8H), 3.51 (m, 4H), 2.61 (m, 4H); MS (m/z): 499 (MH$^+$), 497 (MH$^-$).

EXAMPLE 15

1-[5-(2-Methoxy-benzoyl)-3-pyridin-4-yl-thiophen-2-yl]-piperidin-4-one

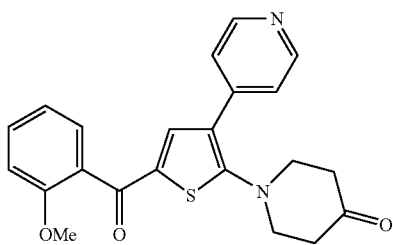

The title product was prepared in 48% yield as a yellow solid according to the procedure described in Example 11 using (2-methoxy-phenyl)-[5-(1,44-dioxa-8-aza-spiro[4.5]dec-8-yl)-4-pyridin-4-yl-thiophen-2-yl]-methanone as starting material. $^1$H NMR (CDCl$_3$) δ 8.62-6.97 (m, 9H), 3.80 (s, 3H), 3.42 (m, 4H), 2.58 (m, 4H); MS (m/z): 393 (MH$^+$), 391 (MH$^-$); HRMS: calc'd MH$^+$ for C$_{22}$H$_{20}$N$_2$O$_3$S 393.1273. Found 393.1289.

EXAMPLE 16

1-[5-(4-Chloro-benzoyl)-3-pyridin-4-yl-thiophen-2-yl]-piperidin-4-one

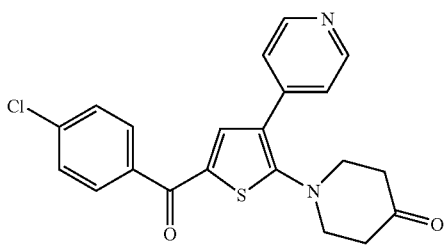

The title product was prepared in 74% yield according to the procedure described in Example 11 using (4-chloro-phenyl)-[5-(1,4-dioxa-8-aza-spiro[4.5]dec-8-yl)-4-pyridin-4-yl-thiophen-2-yl]-methanone as starting material. $^1$H NMR (CDCl$_3$) δ 8.65-7.40 (m, 9H), 3.41 (m, 4H), 2.59 (m, 4H). Ms (m/z): 397 (MH$^+$), 395 (MH$^-$); HRMS: calc'd MH+for C$_{21}$H$_{17}$ClN$_2$O$_2$S 397.0777. Found 397.0767.

Anal. calc'd for C$_{21}$H$_{17}$ClN$_2$O$_2$S, C, 63.55%; H, 4.32%; N, 7.06%. Found, C, 63.29%; H, 4.20%; N, 7.06%.

EXAMPLE 17

1-[5-(4-Nitro-benzoyl)-3-pyridin-4-yl-thiophen-2-yl]-piperidin-4-one

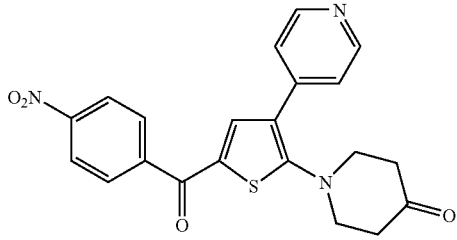

The title product was prepared in 47% yield as a yellow solid according to the procedure described in Example 11 using (4-nitro-phenyl)-[5-(1,4-dioxa-8-aza-spiro[4.5]dec-8-yl)-4-pyridin-4-yl-thiophen-2-yl]-methanone as starting material. $^1$H NMR (CDCl$_3$) δ 8.65-6.97 (m, 9H), 3.24 (m, 4H), 2.60 (m, 4H). Ms (m/z): 408 (MH$^+$), 407 (MH$^-$); HRMS: calc'd MH$^+$ for C$_{21}$H$_{17}$N$_3$O$_4$S 408.1018. Found 408.1024.

EXAMPLE 18

1-(5-Propionyl-3-pyridin-4-yl-thiophen-2-yl)-piperidin-4-one

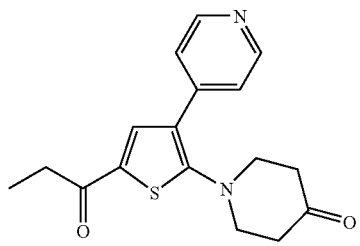

The title product was prepared in 60% yield as a white solid according to the procedure described in Example 11 using 1-[5-(1,4-dioxa-8-aza-spiro[4.5]dec-8-yl)-4-pyridin-4-yl-thiophen-2-yl]-propan-1-one as starting material. $^1$H NMR (CDCl$_3$) δ 8.68 (m, 2H), 7.55 (m, 2H), 3.41 (m, 4H), 2.91 (m, 2H), 2.56 (m, 2H), 1.24 (m, 3H). Ms (m/z): 315 (MH$^+$), 313 (MH$^-$); HRMS: calc'd MH$^+$ for C$_{17}$H$_{18}$N$_2$O$_2$S 315.1167. Found 315.1171.

Anal. calc'd for C$_{17}$H$_{18}$N$_2$O$_2$S, C, 64.94%; H, 5.77%; N, 8.91%. Found, C, 64.16%; H, 5.77%; N, 8.52%.

EXAMPLE 19

1-[5-(3-Bromo-benzoyl)-3-pyridin-4-yl-thiophen-2-yl]-piperidin-4-one

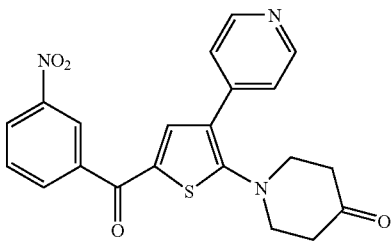

The title product was prepared in % yield according to the procedure described in Example 11 using (3-bromo-phenyl)-[5-(1,4-dioxa-8-aza-spiro[4.5]dec-8-yl)-4-pyridin-4-yl-thiophen-2-yl]-methanone as starting material.

HRMS: calc'd MH+ for $C_{21}H_{17}N_3O_4S$ 408.1018. Found 408.1028.

EXAMPLE 20

1-[5-(3-Bromo-benzoyl)-3-pyridin-4-yl-thiophen-2-yl]-piperidin-4-one

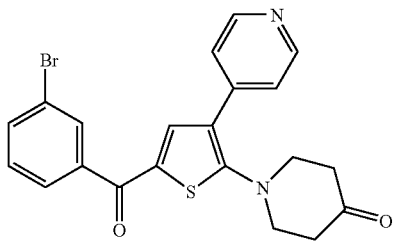

The title product was prepared in 71% yield according to the procedure described in Example 11 using (3-bromo-phenyl)-[5-(1,4-dioxa-8-aza-spiro[4.5]dec-8-yl)-4-pyridin-4-yl-thiophen-2-yl]-methanone as starting material. $^1$H NMR (CDCl$_3$) δ 8.68 (m, 2H), 7.92-7.35 (m, 7H), 3.43 (m, 4H), 2.61 (m, 2H). Ms (m/z): 441 (MH+), 439 (MH−); HRMS: calc'd MH+ for $C_{21}H_{17}BrN_2O_2S$ 441.0272. Found 441.0263.

Anal. calc'd for $C_{21}H_{17}BrN_2O_2S$, C, 57.15%; H, 3.88%; N, 6.35%. Found, C, 57.48%; H, 3.93%; N, 5.97%.

EXAMPLE 21

In Vitro Test

T47D human breast cancer cells are grown in RPMI medium without phenol red (Invitrogen) containing 10% (v/v) heat-inactivated fetal bovine serum (FBS; Hyclone), 1% (v/v) penicillin-streptomycin (Invitrogen), 1% (w/v) glutamine (Invitrogen), and 10 mg/mL insulin (Sigma). Incubation conditions are 37° C. in a humidified 5% (v/v) carbon dioxide environment. For assay, the cells are plated in 96-well tissue culture plates at 10,000 cells per well in assay medium [RPMI medium without phenol red (Invitrogen) containing 5% (v/v) charcoal-treated FBS (Hyclone) and 1% (v/v) penicillin-streptomycin (Invitrogen)]. Two days later, the medium is decanted and the compounds are added in a final concentration of 0.1% (v/v) dimethyl sulfoxide in fresh assay medium. Twenty-four hours later, an alkaline phosphatase assay is performed using a SEAP kit (BD Biosciences Clontech, Palo Alto, Calif.). Briefly, the medium is decanted and the cells are fixed for 30 minutes at room temperature with 5% (v/v) formalin (Sigma). The cells are washed once with room temperature Hank's buffered saline solution (Invitrogen). Equal volumes (0.05 mL) of 1× Dilution Buffer, Assay Buffer and 1:20 substrate/enhancer mixture are added. After 1-hour incubation at room temperature in the dark, the lysate is transferred to a white 96-well plate (Dynex) and luminescence is read using a LuminoSkan Ascent (Thermo Electron, Woburn, Mass.).

TABLE 2

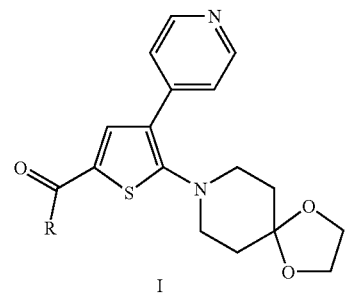

I

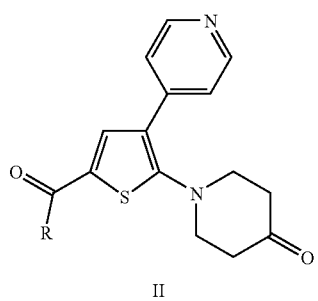

II

| Example # | Structure (I or II) | R | % inhibition |
|---|---|---|---|
| 1 | I | 3,4-di-Cl-phenyl | 6 |
| 2 | I | 4-F-phenyl | 15 |
| 3 | I | 4-Cl-phenyl | 27 |
| 4 | I | 4-NO$_2$-phenyl | 0 |
| 5 | I | Et | 0 |
| 6 | I | Phenyl | 34 |
| 7 | I | 3-MeO-phenyl | 42 |
| 8 | I | 3,5-di-CF$_3$-phenyl | 0 |
| 9 | I | 2-MeO-phenyl | 30 |
| 10 | I | 3-Br-phenyl | 42 |
| 11 | II | Phenyl | 35 |
| 12 | II | 3-MeO-phenyl | 24 |
| 13 | II | 4-F-phenyl | 46 |
| 14 | II | 3,5-di-CF$_3$-phenyl | 57 |
| 15 | II | 2-MeO-phenyl | 39 |
| 16 | II | 4-Cl-phenyl | 30 |
| 17 | II | 4-NO$_2$-phenyl | 30 |
| 18 | II | Et | 26 |
| 19 | II | 3-NO$_2$-phenyl | 29 |
| 20 | II | 3-Br-phenyl | 23 |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of formula (I):

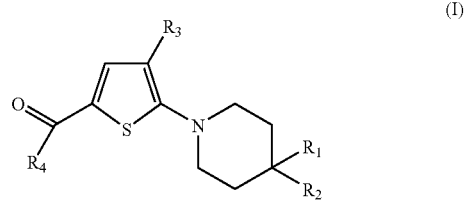

(I)

wherein

R$_1$ and R$_2$ are connected together with the carbon atom to which they are bound via a —O(CH$_2$)$_2$O— linker to form a ring, $R_1$ and $R_2$ are connected together with the carbon atom to which they are bound to form C(O);

$R_3$ is aryl or pyridinyl, optionally substituted by up to three of $R_5$;

$R_4$ is selected from the group consisting of $CH_3CH_2$—, $CH_3CH(CH_3)$, $CH_3CH_2CH_2$—, aryl and pyridinyl, wherein the aryl or pyridinyl is optionally substituted by up to three of $R_5$;

wherein $R_5$ is selected from the group consisting of halogen, $CF_3$, MeO, $NO_2$ and CN;

or a pharmaceutically acceptable salt thereof.

2. The compound of claim 1 selected from the group consisting of

[5-(1,4-Dioxa-8-aza-spiro[4.5]dec-8-yl)-4-pyridin-4-yl-thiophen-2-yl]-(3-methoxy-phenyl)-methanone;

(3-Bromo-phenyl)-[5-(1,4-dioxa-8-aza-spiro[4.5]dec-8-yl)-4-pyridin-4-yl-thiophen-2-yl]-methanone;

1-[5-(4-Fluoro-benzoyl)-3-pyridin-4-yl-thiophen-2-yl]-piperidin-4-one;

1-[5-(3,5-Bis-trifluoromethyl-benzoyl)-3-pyridin-4-yl-thiophen-2-yl]-piperidin-4-one; and 1-[5-(3,5-Bis-trifluoromethyl-benzoyl)-3-pyridin-4-yl-thiophen-2-yl]-piperidin-4-one.

3. A pharmaceutical composition comprising a pharmaceutically acceptable carrier and a therapeutically effective amount of a compound of claim 1.

* * * * *

UNITED STATES PATENT AND TRADEMARK OFFICE
CERTIFICATE OF CORRECTION

| | | |
|---|---|---|
| PATENT NO. | : 7,638,525 B2 | Page 1 of 1 |
| APPLICATION NO. | : 11/255445 | |
| DATED | : December 29, 2009 | |
| INVENTOR(S) | : Jiang et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1002 days.

Signed and Sealed this

Ninth Day of November, 2010

David J. Kappos
*Director of the United States Patent and Trademark Office*